United States Patent [19]

Poore et al.

[11] Patent Number: 5,074,302

[45] Date of Patent: Dec. 24, 1991

[54] SELF-ADJUSTING RATE-RESPONSIVE PACEMAKER AND METHOD THEREOF

[75] Inventors: John W. Poore, South Pasadena; Brian M. Mann, Beverly Hills, both of Calif.

[73] Assignee: Siemens-Pacesetter, Inc., Sylmar, Calif.

[21] Appl. No.: 549,857

[22] Filed: Jul. 9, 1990

Related U.S. Application Data

[63] Continuation-in-part of Ser. No. 301,934, Jan. 25, 1989, Pat. No. 4,940,052.

[51] Int. Cl.$^5$ .............................................. A61N 1/00
[52] U.S. Cl. .............................................. 128/419 PG
[58] Field of Search ........ 128/419 P, 419 PG, 419 PS

[56] References Cited

U.S. PATENT DOCUMENTS

| | | | |
|---|---|---|---|
| 4,899,752 | 2/1990 | Cohen | 128/419 PG |
| 4,940,052 | 7/1990 | Mann et al. | 128/419 PG |
| 4,940,053 | 7/1990 | Mann et al. | 128/419 PG |
| 4,972,834 | 11/1990 | Begemann et al. | 128/419 PG |

*Primary Examiner*—Francis Jaworski
*Assistant Examiner*—George Manuel
*Attorney, Agent, or Firm*—Bryant R. Gold; Lisa P. Weinberg; Malcolm J. Romano

[57] ABSTRACT

A self-adjusting rate-responsive pacemaker includes a conventional programmable pulse generator, a physiological sensor, and a processor, all packaged within an implantable case. The pulse generator generates heart stimulation pulses on demand, or as otherwise programmed, as controlled by a sensor-indicated rate signal. The sensor-indicated rate signal is derived from a raw signal obtained from the physiological sensor, and provides some indication of whether the heart rate should increase or decrease. The processor converts the raw signal to the sensor-indicated rate signal in accordance with a desired relationship (FIGS. 2, 3, 7A, 8). A minimum sensor signal value sets the minimum rate at which the pacemaker generates stimulation pulses, and a maximum sensor signal value sets the maximum rate at which the pacemaker generates stimulation pulses. Both the minimum and maximum sensor signal values may be programmed to automatically be adjusted based on the sensor signals occurring during a prior prescribed time period. In one embodiment, the sensor signals occurring during the prescribed time period are classified into three categories: low, high, and intermediate. The minimum sensor signal value is then computed as the average of the low sensor signals, while the maximum sensor signal is computed as the average of the high sensor signals.

30 Claims, 8 Drawing Sheets

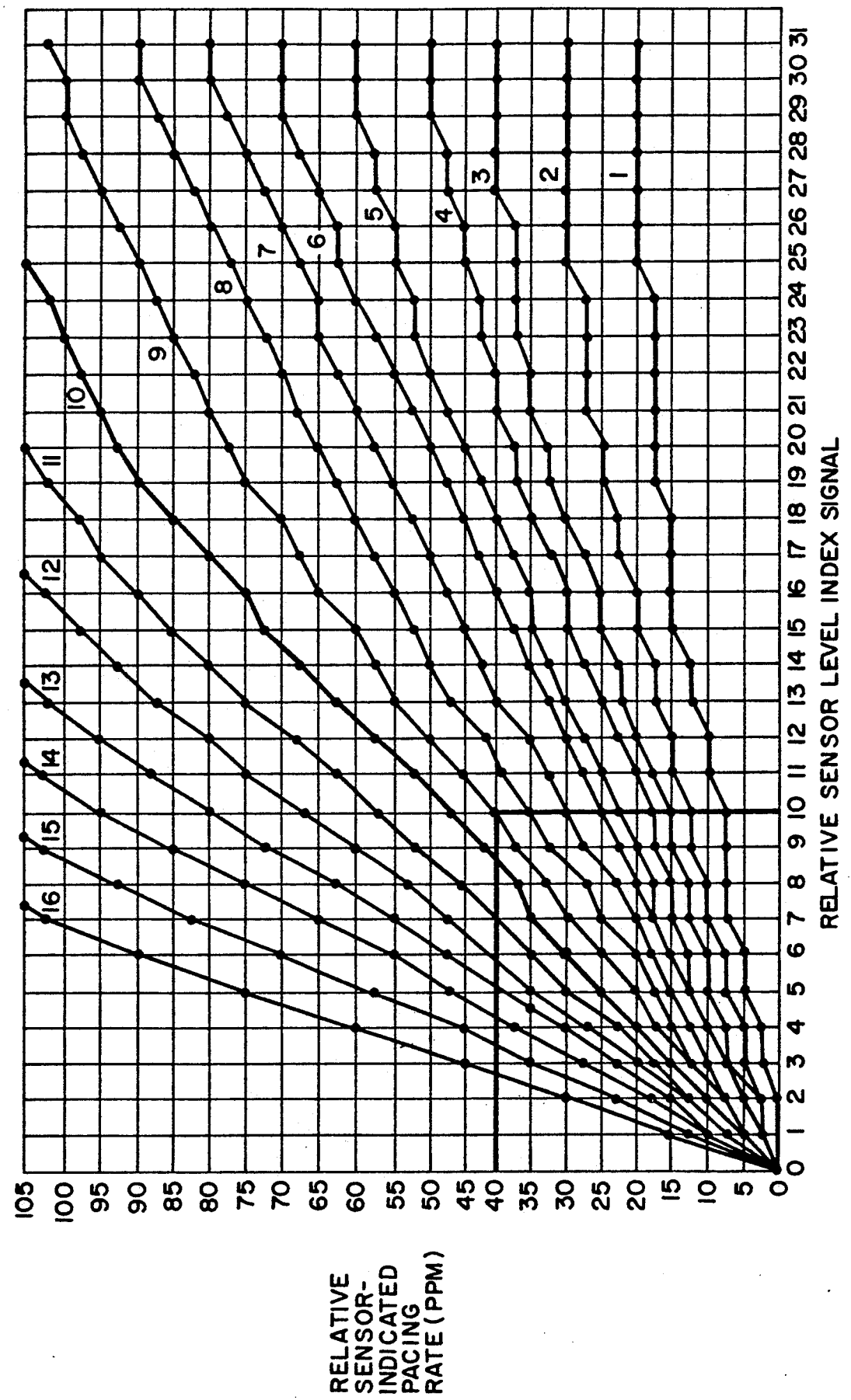

SIGMOID RESPONSE

LOW-END RESPONSE

HIGH-END RESPONSE

SELF-ADJUSTING RATE-RESPONSIVE PACEMAKER AND METHOD THEREOF

This application is a continuation-in-part of application Ser. No. 07/301,934, Jan. 25, 1989, now U.S. Pat. No. 4,940,052, which is incorporated herein by reference.

This application is also related to the following U.S. patent applications, each of which is incorporated in its entirety herein by reference: Ser. Nos. 07/301,935; 07/530,368; and 07/530,369.

BACKGROUND OF THE INVENTION

The present invention relates to cardiac pacemakers, and more particularly to rate-responsive pacemakers. One embodiment of the present invention relates to an implantable microprocessor-controlled rate-responsive pacemaker, or equivalent, wherein the sensor thresholds which define the base rate and/or maximum rate at which pulses are generated on demand, or as otherwise programmed by the pacemaker, is self-adjusting based on the prior activity or inactivity of the patient.

A pacemaker is an implantable medical device that delivers electrical stimulation pulses to a patient's heart, as required, in order to keep the heart beating at a desired rate. Early pacemakers provided stimulation pulses at a fixed rate or frequency, such as 70 pulses per minute (ppm), thereby maintaining the heart beat at that fixed rate. Subsequently, pacemakers were designed to not only stimulate the heart, but also to monitor the heart. If a natural heart beat was detected within a prescribed time period (usually referred to as the "escape interval"), no stimulation pulse was delivered, thereby allowing the heart to beat on its own without consuming the limited power of the pacemaker. Such pacemakers are referred to as "demand pacemakers" because stimulation pulses are provided only as demanded by the heart.

In later pacemakers, stimulation pulses were provided at a programmably selectable rate, and thereafter became commonly known as the "base rate" or minimum rate. If the heart was able to beat on its own at a rate exceeding the programmed base rate, then no stimulation pulses were provided. However, if the heart was not able to beat on its own at a rate exceeding the base rate, then stimulation pulses were provided to ensure that the heart would always beat at least at the programmed base rate. Programmably changing the base rate was accomplished by simply changing the duration of the escape interval.

In recent years, rate-responsive pacemakers have been developed that automatically change the rate at which the pacemaker provides stimulation pulses as a function of a sensed physiological parameter. The physiological parameter provides some indication of whether the heart should beat faster or slower, depending upon the physiological needs of the patient. Thus, for example, if a patient is at rest, there is generally no need for a faster-than-normal heart rate, so the rate-responsive pacemaker maintains the base rate at a normal value, such as 60 ppm. However, if the patient is exercising, or otherwise physiologically active, there is a need for the heart to beat much faster, such as 100 beats per minute. For some patients, the heart is not able to beat faster on its own, so the pacemaker must assist. In order to do this effectively, the physiological need for the heart to beat faster must first be sensed, and the base rate of the rate-responsive pacemaker must be adjusted accordingly. Hence, rate-responsive pacemakers are known in the art that increase and decrease the base rate as a function of sensed physiological need.

Numerous types of sensors are taught in the art for use with a rate-responsive pacemaker. One common type of sensor is an activity sensor that senses the physical activity level of the patient. See, for example, U.S. Pat. No. 4,140,132, issued to Dahl; and U.S. Pat. No. 4,485,813, issued to Anderson. In accordance with the teachings of Dahl or Anderson, a piezoelectric crystal is used as an activity sensor. Such a crystal generates an electrical signal when subjected to physical movement and stress according to well known principles. The electrical signal generated by the crystal is processed by rectifying and filtering it (Dahl), or by monitoring the frequency of the highest amplitude peaks (Anderson). An increase or decrease in the parameter being monitored signals a need to increase or decrease the rate at which pacing pulses are provided. (Note: As used herein, the "pacing rate" refers to the rate at which the pacemaker provides stimulation pulses, or in the case of demand pacemakers, the rate at which the pacemaker would provide stimulation pulses in the absence of naturally occurring heart beats.)

Other types of sensors used in prior art rate-responsive pacemakers include sensors that sense respiration rate, minute volume, blood oxygen level, blood and/or body temperature, blood pressure, the length of the Q-T interval, the length of the P-R interval, etc. Rate-responsive pacemakers using these other types of sensors have yet to demonstrate their commercial viability. To applicants' knowledge, only the piezoelectric sensor has been marketed successfully in significant numbers to date. However, any or all of the prior art sensors previously mentioned, or any other sensors, may prove efficacious in the future. Advantageously, the invention presented herein can be used with any of these prior art sensors, or with any physiological sensors yet to be developed.

Even when a physiological sensor is used in a rate-responsive pacemaker, however, there is still a need to customize the manner in which a particular patient reacts to the output signals from the chosen sensor. While some flexibility exists in this regard in the manner in which the pacemaker is programmed, the available programming options relative to the rate-responsive features have heretofore been severely limited. Further, even when initially programmed in a suitable manner, there is no guarantee that this manner of programming will remain suitable over a long period of time. Further, while reprogramming can typically be performed, such reprogramming requires additional visits to the doctor, which visits can become quite burdensome for the patient. Hence, there is a need in the art for a rate-responsive pacemaker that provides greater flexibility in the manner in which the pacemaker is initially programmed, and that thereafter provides automatic adjustment of some of the key parameters that influence the effectiveness thereof.

Moreover, because all rate-responsive pacemakers include some type of sensor or sensing mechanism to sense at what rate the heart should be paced, there is a critical need to ensure that the sensor, and its related circuitry, function properly. Should the sensor fail, or should any of the circuits associated with the sensor fail, the pacemaker must still continue to provide stimulation pulses, if required, at a safe rate. In this regard, it is noted that normally, because of the stringent design and manufacturing requirements imposed on an implantable medical product, failure of the pacemaker or the pacemaker circuits and elements is an extremely unlikely event. However, because the sensors used with a rate-responsive pacemaker involve additional parts typically of lower reliability than that of the pacemaker's basic non-rate-responsive pacing circuitry, and because the operation of such sensors typically involves measuring or sensing very ill-defined and/or low level signals, and further because the processing circuitry used with such sensors is often by necessity quite sophisticated and complex (in order to extract the relevant information from the low level signals that are sensed), the possibility of a circuit failure in a rate-responsive pacemaker increases. Hence, what is needed in the art is a fail-safe mechanism within the rate-responsive pacemaker that can be used to provide stimulation pulses at a safe rate in the event of failure of the sensor and/or rate-responsive portions of the pacemaker circuits.

SUMMARY OF THE INVENTION

The present invention provides a versatile rate-responsive pacemaker that addresses the needs identified above as well as other needs. In one embodiment, the rate-responsive pacemaker of the present invention includes an otherwise conventional programmable pacemaker chip, a microprocessor chip, a physiological sensor, and a battery, all housed within the same implantable enclosure. The programmable pacemaker chip provides all of the conventional programmable pacemaker functions, including generating pacing pulses in one of many possible modes of operation, sensing cardiac activity from one or both chambers of the heart, and providing a selected programmed response. The microprocessor chip includes a powerful processing means for interfacing between the physiological sensor and the control circuits of the pacemaker chip. Such processor generates a sensor-indicated rate signal that varies as a function of a raw signal obtained from the sensor. Such sensor-indicated rate signal, if programmably selected to be used by the pacemaker circuits (SENSOR ON), provides a basis for automatically adjusting the pacing rate of the pacemaker as a function of the physiological needs sensed by the sensor. If not selected (SENSOR OFF), the pacemaker provides a pacing rate as programmed in conventional manner. Thus, the present invention provides fail-safe mechanism, wherein stimulation pulses are provided by the programmable pacemaker chip by selecting SENSOR OFF in the event of a failure of the sensor and/or rate-responsive portions of the pacemaker circuits.

In one embodiment, the processor means includes: pre-processing means for converting the raw sensor signal to one of a plurality of sensor level index signals; and conversion means for converting the sensor level index signal to a sensor-indicated rate signal. The sensor-indicated rate signal is converted by a selected one of a family of transfer characteristic curves, or tables, each curve or table relating the sensor level index signal on one axis to the sensor-indicated rate signal on the other axis. For sensor level index signals below a prescribed lower threshold, the sensor-indicated rate signal provides stimulation pulses at a base rate. The sensor-indicated rate signal for sensor level index signals above a prescribed upper threshold provides stimulation pulses at a maximum rate. However, the prescribed lower and upper thresholds as thus described are not necessarily fixed. Rather, they may be independently and automatically self-adjusting based on the sensor level signals sensed for the patient during a prior prescribed time period. Advantageously, this self-adjusting of the lower and upper thresholds also automatically defines the end points of the transfer curve. Since, in the preferred embodiment the transfer curve is linear between the lower and upper thresholds, the automatic self-adjustment of the thresholds eliminates the need for the physician to program the slope, thereby simplifying the number of programmable parameters and minimizing the number of reprogrammings that may occur at follow-up.

In the preferred embodiment of the invention, the sensor is a piezoelectric sensor bonded to the inside of the pacemaker enclosure. This sensor generates a raw signal which results from deflections of the enclosure occurring with patient activity. However, other types of physiological sensors may also be used, e.g., sensors that sense various physiological parameters associated with the need to adjust the heart rate of the patient. Such sensors may include, in addition to a physical activity sensor described above, e.g., a blood oxygen sensor, a respiration rate sensor, a temperature sensor, a timing sensor that senses various intervals associated with the heart (such as the P-R interval, or the QRS-T interval), and others. The present invention advantageously may be used with whatever type of sensor is desired.

To illustrate, a typical patient may have a base rate of 60 ppm (pulses per minute) and a maximum SIR of 150 ppm. Thus, regardless of how physiologically inactive the physiological sensor senses the patient to be, such a pacemaker always provides stimulation pulses on demand at a rate of at least 60 ppm. Similarly, regardless of how physiologically active the physiological sensor senses the patient to be, the pacemaker provides stimulation pulses on demand at a rate no greater than 150 ppm. For activity levels intermediate these two extremes, the pacemaker provides stimulation pulses on demand at rates controlled by the prescribed transfer function. Advantageously, an important feature of the present invention provides for the automatic self-adjustment of the lower sensor level threshold and upper sensor level threshold values as a function of the patient's prior physiological activity, as sensed over some prior interval of time.

The lower and upper thresholds of the sensor level signal above and below which the rate-responsive functions become effective can, of course, be programmably set to any desired value. In the selfadjusting embodiment, however, the lower threshold is set automatically based upon an average, or other processed value, of selected physiological data (obtained from the physiological sensor) of the patient over a prescribed period of time. For example, the lower threshold average may be computed over a 24-hour period in which the overall average indicates the patient's rest level (i.e., the patient only has small intervals at high activity and over 24 hours is considered primarily at rest). Alternately, the lower threshold average may be computed only after removing periods of high activity from the physiological activity data. Similarly, the upper threshold may be determined automatically, based upon an average or other processed value of other selected physiological data, only after removing periods of low activity.

Thus, memory circuits included within or connected to the microprocessor chip of the rate-responsive pacemaker allow data to be stored or processed relative to the past performance of the rate-responsive pacemaker. These memory circuits can be noninvasively interrogated and the data displayed as a histogram which shows the distribution of the sensor-indicated rate data over the recording period. Advantageously, this data may be subsequently studied by appropriate medical personnel, at a time convenient to all concerned, to verify that the pacemaker is optimally programmed and/or functioning within expectations. Alternatively, as indicated, in one embodiment, such data can be used by the on-board processing circuits to automatically adjust the sensor threshold levels corresponding to the programmed base rate, the maximum sensor-indicated rate, and other key parameters associated with the operation of the rate-responsive portions of the pacemaker circuits.

Thus, one feature of the rate-responsive pacemaker herein described allows the threshold at which the rate-responsive functions of the pacemaker take effect to be selectively and automatically adjusted to suit the needs of a particular patient. Coupled with this threshold-setting ability is the capability of programmably selecting a particular response characteristic, such as the rate at which the sensor-indicated rate changes as a function of sensed changes in the signal from the sensor (slope), how quick the sensor-indicated rate starts to change (reaction time), and how rapidly the sensor-indicated rate returns to a normal level (recovery time).

More particularly, one embodiment of the present invention allows the lower threshold and upper threshold of the selected transfer function of the rate-responsive pacemaker to be automatically set based upon the sensed physiological activity level of the patient over a prior period of time, such as the previous 12 or 36 hours.

It is a feature of the rate-responsive pacemaker of the present invention to monitor the sensed physiological activity level over a prescribed period of time, regardless of whether the SENSOR ON or SENSOR OFF mode of operation is selected.

It is a further feature of the present invention to provide a rate-responsive pacemaker that provides a desired pacemaker response to the signals generated by a physiological sensor, yet a response that can be easily altered during design, manufacturing, testing or patient-use phases.

The invention described herein further contemplates a method of automatically adjusting the maximum and minimum threshold values based upon prior sensed physiological data. Such self-adjusting method includes the steps of: (a) monitoring the sensor level signals obtained from the physiological sensor over a prescribed period of time; (b) computing an average, or other processed value; and (c) using this computed value to automatically set the minimum threshold, of the sensed physiological data, wherein pacing pulses are generated on demand at a rate determined by the value of the sensor-indicated rate signal when the sensor signals are above the adjusted minimum threshold signal and at a base rate when the sensor signals are below the adjusted minimum threshold signal. The method further includes separating the sensor level signals into at least a low physiological activity category and a high physiological activity category, separately computing an average of the low and high physiological activity sensor levels and using these values to automatically set the minimum and maximum thresholds for the transfer curve which describes the relationship between the sensor level index and the sensor-indicated rate signal.

BRIEF DESCRIPTION OF THE DRAWINGS

The above and other aspects, features and advantages of the present invention will be more apparent from the following more particular description thereof presented in conjunction with the following drawings wherein:

FIG. 3 illustrates a preferred family of transfer curves used with the present invention in order to provide a selection of different slopes;

DETAILED DESCRIPTION OF THE INVENTION

The following description presents the best mode presently contemplated for practicing the invention. This description is not to be taken in a limiting sense but is made merely for the purpose of describing the general principles of the invention. The scope of the invention should be ascertained with reference to the claims.

The present invention is best understood with reference to the drawings, wherein like numerals are used to represent like parts or elements throughout.

Figure 1:
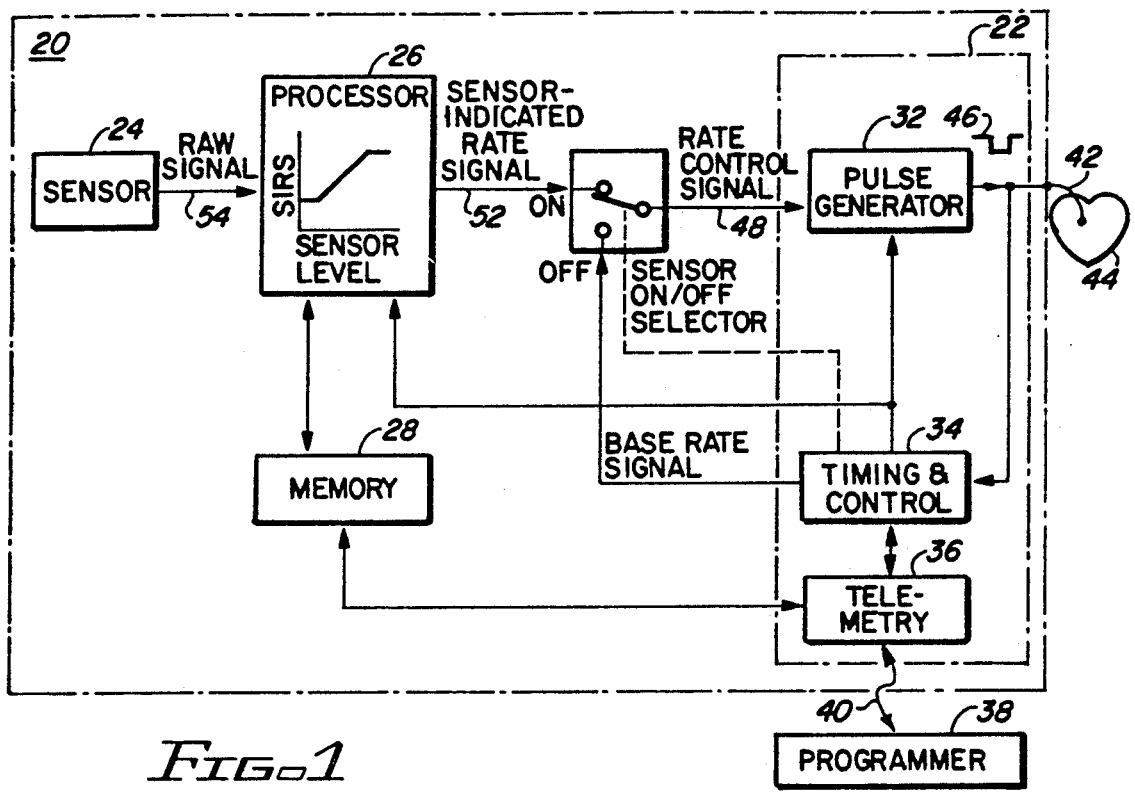
FIG. 1 is a functional block diagram of a rate-responsive pacemaker incorporating the features of the present invention.

As an outline and overview of the description that follows, a functional description of one embodiment of the rate-responsive pacemaker will first be presented (FIG. 1). This functional description is used to teach the basic operating principles of the invention, including the various programmable and automatic control parameters that may be used therewith, such as slope, threshold, reaction time and recovery time (FIGS. 2–5).

For a patient having a rate-responsive pacemaker, it is a function of the pacemaker to be able to sense a change in the physiological demands placed on the patient and to adjust the rate at which stimulation pulses are provided to the heart accordingly. To this end, the rate-responsive pacemaker employs some type of physiological sensor, as previously described. The most common type of sensor, which mimics a physiological response, is the physical activity sensor, e.g., a piezoelectric crystal that senses physical forces and converts such to an electrical signal. However, numerous other types of physiological sensors, or combinations of such sensors, may also be used.

Referring first to the functional block diagram of FIG. a rate-responsive pacemaker 20 configured in accordance with the teachings of the present invention is shown. The pacemaker 20 includes a conventional pacemaker chip 22, a sensor 24, a processor 26, memory circuit 28, and a selection means 30. The conventional pacemaker chip 22 includes at least a pulse generator 32, timing and control circuits 34, and telemetry circuits 36. The pulse generator 32 includes at least one lead 42 that provides an electrical contact with the patient's heart 44. An external programmer 38 is also used to send programming signals to the telemetry circuits 36. These programming signals are depicted symbolically as the wavy line 40 in FIG. 1. It is noted that such signals may be sent bidirectionally either from the programmer 38 to the pacemaker 20, or from the pacemaker 20 to the programmer 38.

Functionally, the pulse generator generates stimulation pulses 46 at a rate determined by a rate control signal, appearing on signal line 48. These pulses, in turn, are delivered to the heart 44 through the lead 42 in conventional manner. This lead 42 may be either a unipolar lead, bipolar lead, or other multi-pole lead as is known in the art. Further, although the sensor 24 is shown in FIG. as being included within the pacemaker 20, it is to be understood that the sensor 24 could also be included within, or coupled to, the lead 42; or otherwise placed external to the pacemaker 20.

The lead 42 also presents electrical signals occurring within the heart 44, such as P-waves and R-waves (evidencing natural cardiac activity of the atria and ventricles, respectively), to the timing and control circuits 34. Hence, for example, when programmed in a demand mode of operation, the pacemaker chip 22 is able to inhibit the generation of a pacing pulse 46 when natural cardiac activity is sensed within a designated time period, in conventional manner.

A more complete description of the pacemaker chip 22 and its operation may be found in other documents. For example, U.S. Pat. Nos. 4,686,988 and 4,712,555, disclose the primary components of a conventional pacing system and teach the basic operation thereof. U.S. Pat. Nos. 4,686,988 and 4,712,555 are incorporated herein by reference.

In operation, the rate-responsive pacemaker 20 may operate in either a SENSOR ON mode or a SENSOR OFF mode. The selection of a desired mode of operation is controlled by the selector 30, shown functionally in FIG. 1 as a switch. The selector 30 connects a base rate signal on signal line 50 or a sensor-indicated rate signal on signal line 52 to the rate control signal line 48 of the pulse generator 32. Control of the selector 30 is obtained from the timing and control circuits 34, which control can be selected by an appropriate programming signal received from the programmer 38.

When the SENSOR OFF mode is selected, the selector 30 directs the base rate signal, generated by the timing and control circuits 34, to the rate control signal line 48 of the pulse generator 32. This base rate signal thus controls the pacing rate of the pacemaker 20 in conventional manner.

Typically, the rate control signal 48 may be thought of as simply a signal responsible for generating a trigger pulse at the timing out of an escape interval (also generated by the timing and control circuits 34). However, if natural cardiac activity is sensed during the escape interval, no trigger pulse is generated and the timing circuits responsible for generating the escape interval are reset, thereby starting a new escape interval. Hence, regardless of the source of the rate control signal 48 (either the base rate signal 50 or the sensor-indicated rate signal 52), such signal can be overridden (if the pacemaker 20 is so programmed) by the sensing of natural cardiac activity.

When the SENSOR ON mode is selected, the rate control signal 48 of the pulse generator 32 is connected by way of selector 30 to the sensor-indicated rate signal line 52 obtained from the output of processor 26. The sensor-indicated rate signal is derived from a raw signal obtained from the sensor 24. Typically, the processor 26 includes means for converting the raw signal, appearing on signal line 54, to a sensor level index signal. This conversion may be accomplished in various ways, but typically a desired transfer characteristic, converting the sensor level index signal to an appropriate sensor-indicated rate signal, is stored or programmed into the memory 28 and used by the processor 26 to effectuate the conversion.

Figure 2:
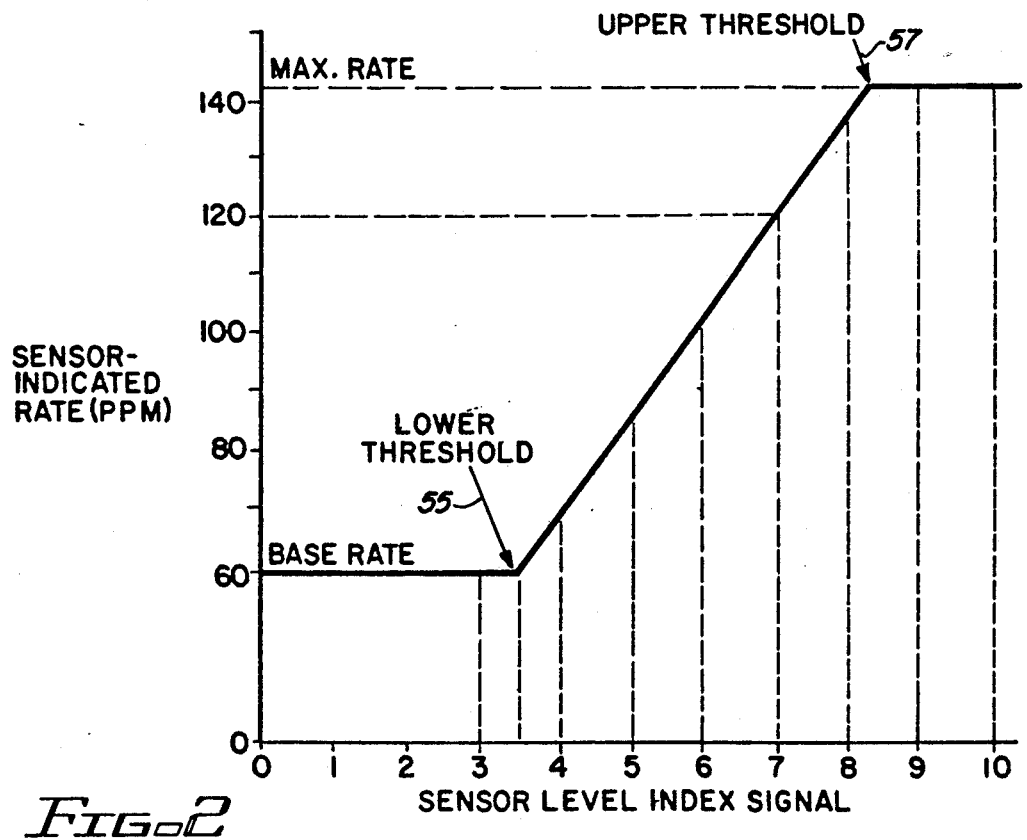
FIG. 2 is a transfer curve illustrating the general relationship between a sensor index signal and a sensor-indicated rate signal.

Referring next to FIG. 2, a typical transfer characteristic of a rate-responsive pacemaker is illustrated. As drawn, the vertical axis represents the sensor-indicated rate (SIR) signal. The horizontal axis represents a particular sensed parameter, or combination of sensed parameters, used to control the pacemaker. The horizontal axis is divided into equal increments, corresponding to different sensor levels obtained from the sensor 24. These increments are identified as "sensor level index signals." (The terms "sensor index signal", "sensor level signal" or "sensor level index," as used herein, are all meant to be synonymous with the term "sensor level index signal.")

In the preferred embodiment, the sensor level signals are the computed average amplitude of the raw signal 54. For a complete description of the computation of the average amplitude, see co-pending application "AVERAGE AMPLITUDE CONTROLLED RATE RESPONSIVE PACEMAKER HAVING AUTOMATICALLY ADJUSTABLE CONTROL PARAMETERS," filed 5/30/90, Ser. No. 07/530,369, which application is incorporated herein by reference.

Briefly, the raw sensor signal is an analog signal having a wide and varied amplitude and frequency associated therewith. This signal is rectified and filtered, providing an analog signal level that varies as a function of the average amplitude over time, or other desired parameter, of the raw signal. This analog signal is then converted to an appropriate digital signal.

The number of sensor level index signal increments could be readily altered by those skilled in the art depending upon the particular sensitivity desired relative to changes in the raw signal from the sensor 24. It is believed that most applications would require at least ten index levels, as shown in FIG. 2, but certainly as few as four index levels could be used and still provide some measure of physiological control of the pacemaker. Each increment of the sensor level index signal may be a uniform fractional increase of the average amplitude of the raw sensor signal. For example, if ten sensor level index signals are used, a sensor level index signal of 1 represents that the raw sensor signal contains 1/10 of its maximum possible value, a sensor level index signal of 2 represents 2/10 of the maximum possible value, and so on. Alternately, the average amplitude of the raw signal may be effectively divided into zones, which zones may or may not represent equal amounts of average amplitude. Each incremental sensor level index signal is assigned to a particular zone. Thus, if the average amplitude of the raw signal is determined to fall into zone 3, for example, the sensor level index signal is assigned a value of 3.

It is seen that the pacing rate indicated by the particular transfer relationship shown in FIG. 2 for any sensor level index value less than lower threshold 55 is fixed at the base rate, or minimum rate, which is in FIG. 2 set to 60 ppm. Below the lower threshold 55, the sensor-indicated rate signal does not decrease below the base rate. As shown in FIG. 2, the lower threshold 55 has a sensor level index value of about 3.5. However, where only discrete values of the sensor level index signal are employed, as in a digital system, the lower threshold is effectively three.

In FIG. 2, it is seen that sensor level index signals having a value of four through eight define a sensor-indicated rate signal that varies as a function of the transfer curve. For example, a sensor index of seven in FIG. 2 defines a sensor-indicated rate signal of 120 ppm. Sensor level index signals in excess of nine define a maximum rate for the pacemaker. The point at which this maximum rate begins is identified as the upper threshold 57. For the example shown in FIG. 2, the upper threshold has an effective value of nine (assuming discrete index level signals). (A further explanation of the rate-responsive transfer curve and the various parameters that can be adjusted thereon is presented below in connection with FIG. 7A.)

FIG. 3 describes a "relative" or "normalized" family of transfer curves for use with one preferred embodiment of the present invention. The horizontal axis of FIG. 3 is labeled "Relative Sensor Level". This horizontal axis corresponds to the sensor level index signal described above in FIG. 2, wherein "0" corresponds to the lower threshold, and the relative sensor levels are added to the lower threshold to obtain the absolute values shown in FIG. 2. The vertical axis of FIG. 3 is identified as the "Relative Pacing Rate." This vertical axis corresponds to the sensor-indicated rate signal described above in FIG. 2, wherein "0" corresponds to the base rate, and the relative pacing rate is added to the base rate to obtain the absolute values shown in FIG. 2. As defined in FIG. 3, relative pacing rates of from 0 to 105 ppm are shown. For example, if the base rate is programmed to be 60 ppm, and if the relative sensor level (index signal) is ten above threshold, and if curve number 9 is chosen as the defining curve, then the pacing rate increase is 40 ppm above base rate. This means that the sensor-indicated rate signal would be 100 ppm (the base rate plus the relative rate: 60 ppm+40 ppm=100 ppm).

A particular curve of the family of transfer curves is selected by programming a parameter termed "slope". The programmed slope value determines the increase in pacing rate (above the programmed base rate) which will occur at various levels of patient activity above activity threshold. As illustrated in FIG. 3, there are sixteen programmable slope values that define the increases in pacing rate which occur for all possible sensor level index signals. In general, low sensor level index signals correspond to low levels of physiological activity, whereas high sensor level index signals correspond to high levels of physiological activity. Higher slopes result in a greater increase in pacing rate than do lower slopes for any specific sensor level index (level of patient activity). Thus, by selecting an appropriate slope, the response of the pacemaker to a particular level of patient activity can be customized to suit the individual needs of a particular patient.

In order to prevent inappropriate increases in pacing rate while the patient is at rest or at low levels of activity, one embodiment of the rate-responsive pacemaker of the present invention offers a plurality of programmable threshold values that may be selected. In general, as described above in connection with FIG. 2, "threshold" may be thought of as that sensor level which must be exceeded before the rate-responsive functions of the pacemaker take effect. That is, for sensor levels below the threshold, the sensor-indicated rate signal remains fixed at the base rate (meaning that the relative sensor-indicated rate signal is zero). In order to provide a programmable threshold, an "offset" value is used. Conceptually, offset is like a bias signal that is subtracted from the raw sensor signal level in order to effectively shift the break point of the transfer curve in a desired direction. Use of an offset value in this manner to set a threshold value thus defines a selectable minimum level of patient activity which must occur before the sensor-indicated pacing rate increases above the programmed base rate.

Figure 4A:
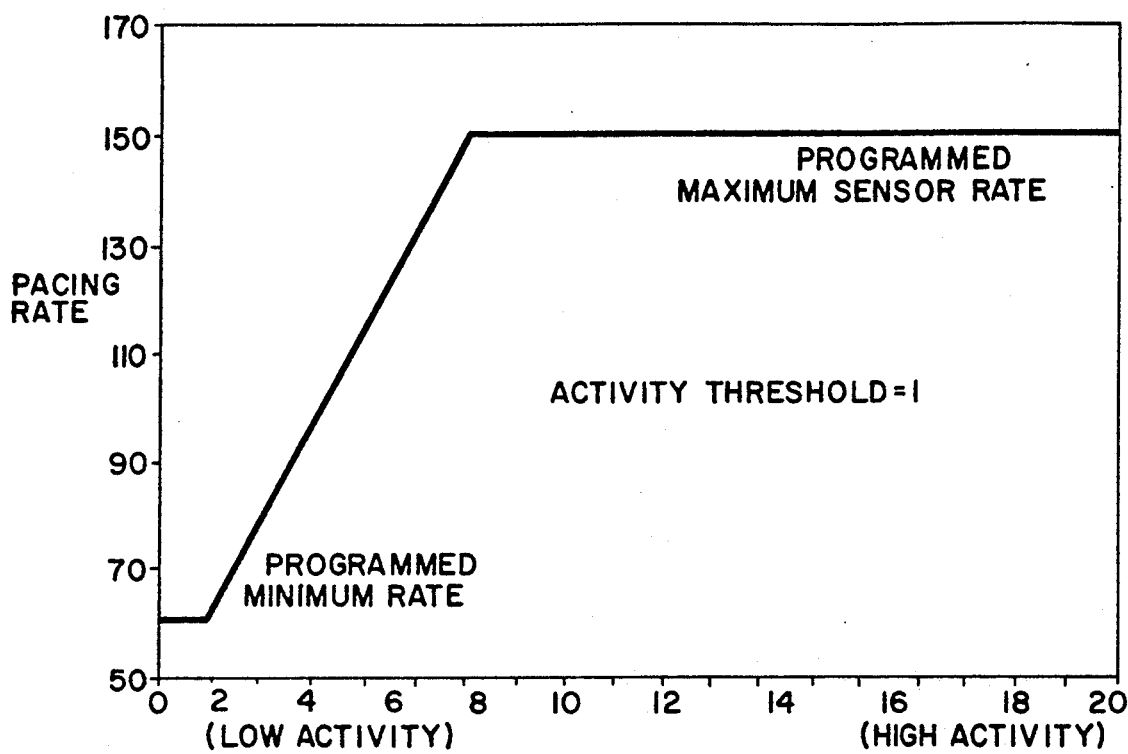
FIGS. 4A and 4B are transfer curves used to teach the concept of a programmable and automatic threshold.
Figure 4B:
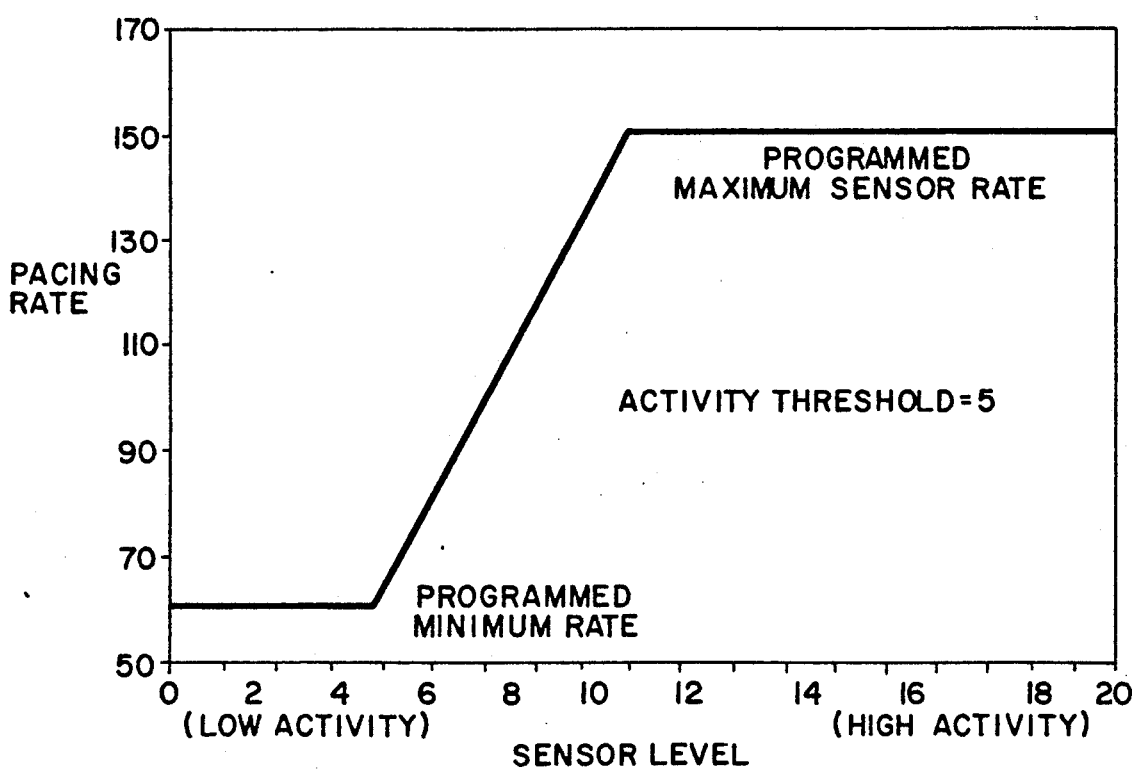

The effect of altering the lower threshold 55 is illustrated in FIGS. 4A and 4B. At a threshold value of 1, for example, the transfer relationship shown in FIG. 4A effectively results. This particular relationship allows increases in pacing rate to be observed at fairly low levels of patient activity. (For example, a sensor level index signal of two or higher allows the pacing rate to increase.) However, if a threshold value of five is selected, as shown in FIG. 4B, a much higher level of patient activity is required before an increase in pacing rate is observed (sensor level index signals of six or greater are needed).

Figure 5A:
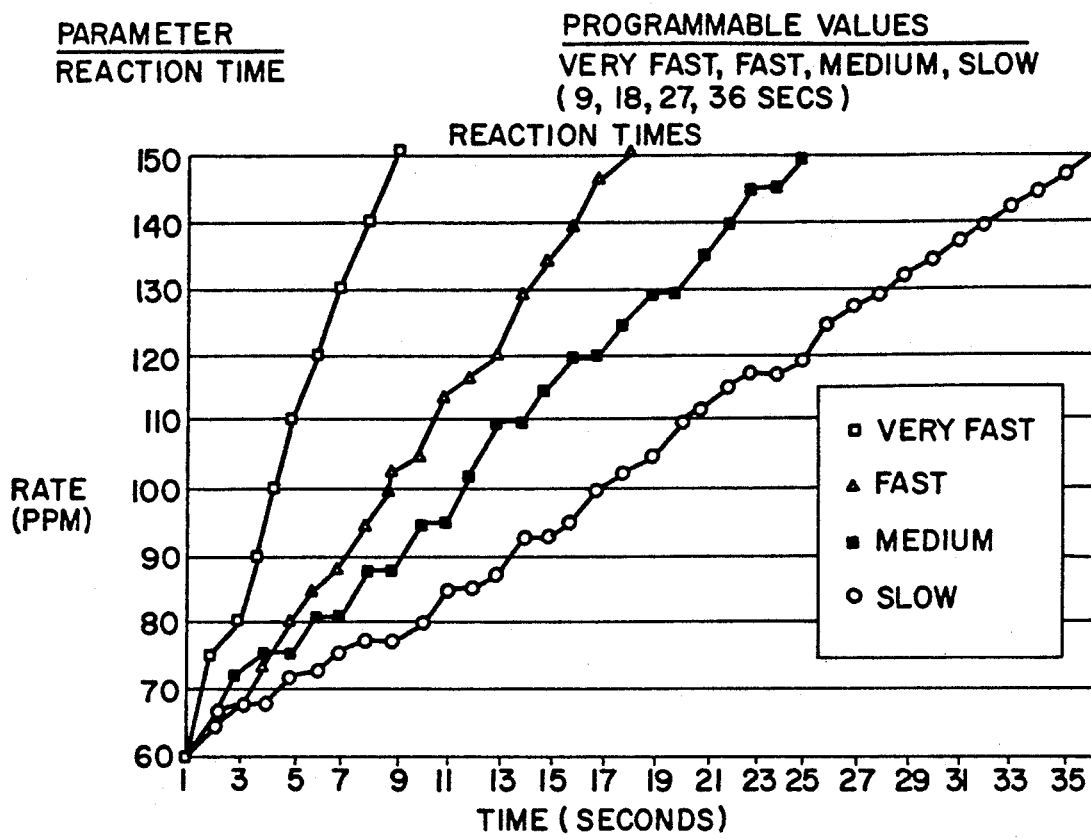
FIG. 5A is a graph that illustrates the various reaction times used with the present invention.

In FIG. 5A, the concept of reaction time is presented. Reaction time is the minimum time allowed for an increase in pacing rate from the programmed basic rate to the programmed maximum rate. A short reaction time allows the pacing rate to increase rapidly in response to patient activity, whereas a long reaction time forces a slow increase in pacing rate. As seen in FIG. 5A, four programmable reaction times are provided in the preferred embodiment of the invention. (More or less than this number of reaction times could, of course, also be included.) These are identified as "very fast," "fast," "medium," and "slow." FIG. 5A illustrates the change in pacing rate versus time in response to a sudden increase to maximum activity level for the four programmable reaction times. It is noted that the programmed reaction time only applies to increases in pacing rate resulting from sensor detected activity. Reaction time has no effect when the pacemaker is operating in a non-rate-responsive mode.

Figure 5B:
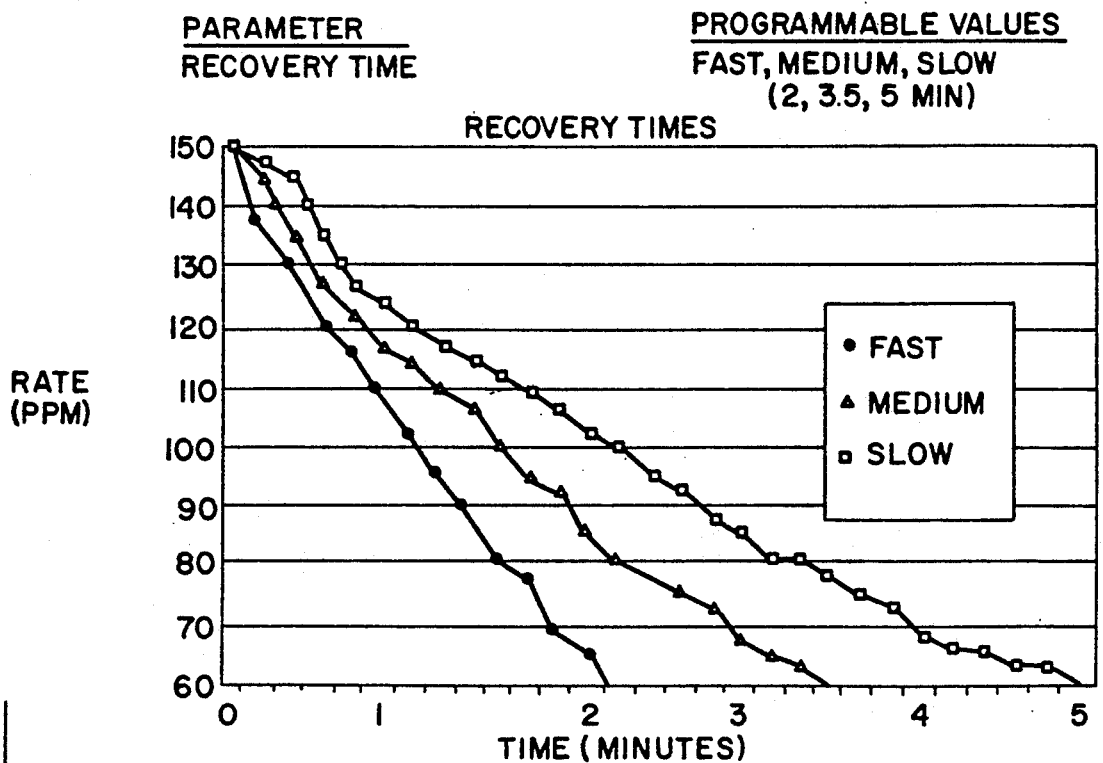
FIG. 5B is a graph that shows the recovery times used with the pacemaker of the present invention.

Similar to the concept of reaction time is "recovery time." Recovery time determines the minimum time required for a decrease in the pacing rate from the programmed maximum rate to the programmed basic rate. This feature advantageously prevents abrupt decreases in pacing rate concurrent with the conclusion of sensed patient activity. As shown in FIG. 5B, there are three values of recovery time that can be programmably selected in the preferred embodiment of the invention: fast, medium and slow. A long or slow reaction time results in a slow decrease in pacing rate when the patient's activity level decreases. A short or fast reaction time allows the pacing rate to decrease more rapidly. FIG. 5B illustrates changes in the pacing rate versus time in response to a sudden decrease in activity for each of the three programmable recovery times. As with reaction times, the set recovery times apply only to decreases in pacing rate resulting from sensor detected activity. The recovery time selected will not affect pacing rate when the pacemaker is operating in a non-rate-responsive mode, such as during tracking or triggered operation.

The present invention provides for the auto-or self-adjustment of the lower and upper thresholds 55 and 57 (FIG. 2). Before explaining this particular feature of the invention, however, it will be helpful to provide additional background information relating to rate-responsive pacing.

Figure 6:
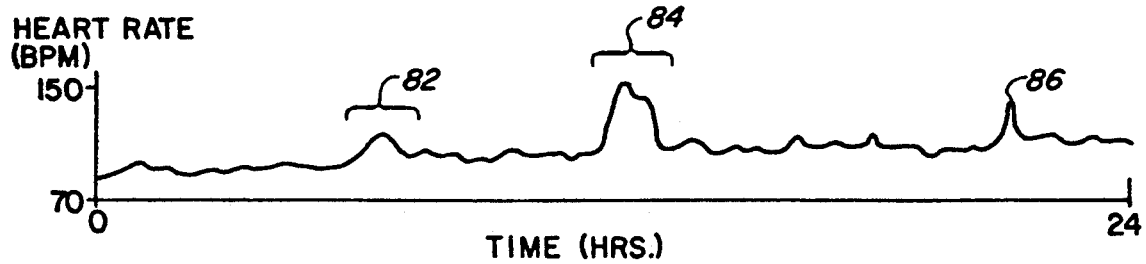
FIG. 6 shows how the physiological activity of a typical patient may vary over a 24 hour period.

In FIG. 6, variations in the sensor-indicated heart rate of a typical patient over a 24 hour period of time are shown. Such heart rate variations may be measured, e.g., with a Holter monitor, or equivalent. Further, it is noted that many modern implantable pacemakers include sufficient memory for storing sensor-indicated heart rate data, such as that shown in FIG. 6, over a relatively long period of time. As seen in the example of FIG. 6, during most of the 24 hour period, the patient's sensor-indicated heart rate assumes a low value, on the order of 70 bpm (beats per minute). This may be considered the "rest" rate for this particular patient, and represents those periods of time throughout the 24 hour period when the physiological demands of the patient are low. Such periods of time may correspond to periods of sleep, sitting (e.g., at home, at an office, or in a car or train), and other times of relative inactivity. During some relatively short portions of the 24 hour period, the heart rate increases appreciably. For example, during the time identified by the reference numeral 82, the heart rate experiences a modest increase. This may be due, e.g., to the patient's walking to or from a bus/train terminal. In contrast, during the time identified by the reference numeral 84, the heart rate experiences a major increase. This may be due, e.g., to a period of strenuous exercise, such as swimming, cycling, jogging, or the like. At time 86, another noticeable increase in the heart rate occurs for a very short period of time. This short abrupt increase could be caused by any sudden physiological demand placed on the patient's body due to exercise, emotional or mental stress. Thus, as seen in FIG. 6A, the typical patient experiences varying heart rates over the 24 hour period, which varying heart rates adapt to meet the physiological demands placed on the patient.

Advantageously, the present invention provides for the automatic setting of the lower threshold 55 and upper threshold 57 based on the sensor levels measured over a prescribed interval. Thus, the "autothreshold" feature eliminates the need to manually select activity threshold and the slope or transfer curve. When the autothreshold feature is selected, the activity threshold at any particular point in time is determined by the processor 26 (FIG. by adding the average sensor level index signal over a prescribed prior period of time to a prescribed threshold offset value. For example, if the prescribed prior period of time is the preceding 12 hours with an average sensor level index signal of one (1) during these 12 hours and the prescribed threshold offset is one (1), then the threshold offset is automatically set to two (2).

In one embodiment, the lower threshold 55 is automatically determined by recognizing that nearly all patients will be at a relatively low level of activity for most of any 12 to 36-hour period. The memory circuits 28 (FIG. thus continuously record the average sensor level for the prior 12-hour period (or other prescribed time period). This running average is continuously updated with new sensor levels that are measured every pacing cycle. Each reading of the individual sensor has only a small effect on the average because of the large number of pacing cycles which occur in the prescribed time.

The autothreshold feature of the invention may be initialized from an external programmer 38. An initial value of the Automatic Threshold may be determined by running the pacing algorithm for 30 pacing intervals in order to develop a 30 cycle sensor average. Thereafter, as more sensor data is made available, the sensor level index signal is averaged over a prescribed period of time (much longer than 30 cycles, preferably long enough to be predominated by low level activity, such as 18 hours) in order to provide a continuous indication of what the threshold value should be. The threshold value is set at this long-term running average with an appropriate offset added thereto.

Other measures of the sensor level index signal, in addition to, or in place of, an average signal, could also be used. In the preferred embodiment, a weighted average of the index signals is performed, giving greater weight to the index signals from certain time periods of the day or within certain sensor level ranges. Further, a least squares computation could be performed wherein sensor level index values having a large variance from other sensor level index values are discounted. In other words, any processing method or technique that provides a meaningful measure of the variation and movement of the sensor level index over the time period of interest may be used. This measure of movement may be thought of as a type of reference sensor level signal representative of all, or most all, sensor level signals occurring during the desired time period.

Figure 7A:
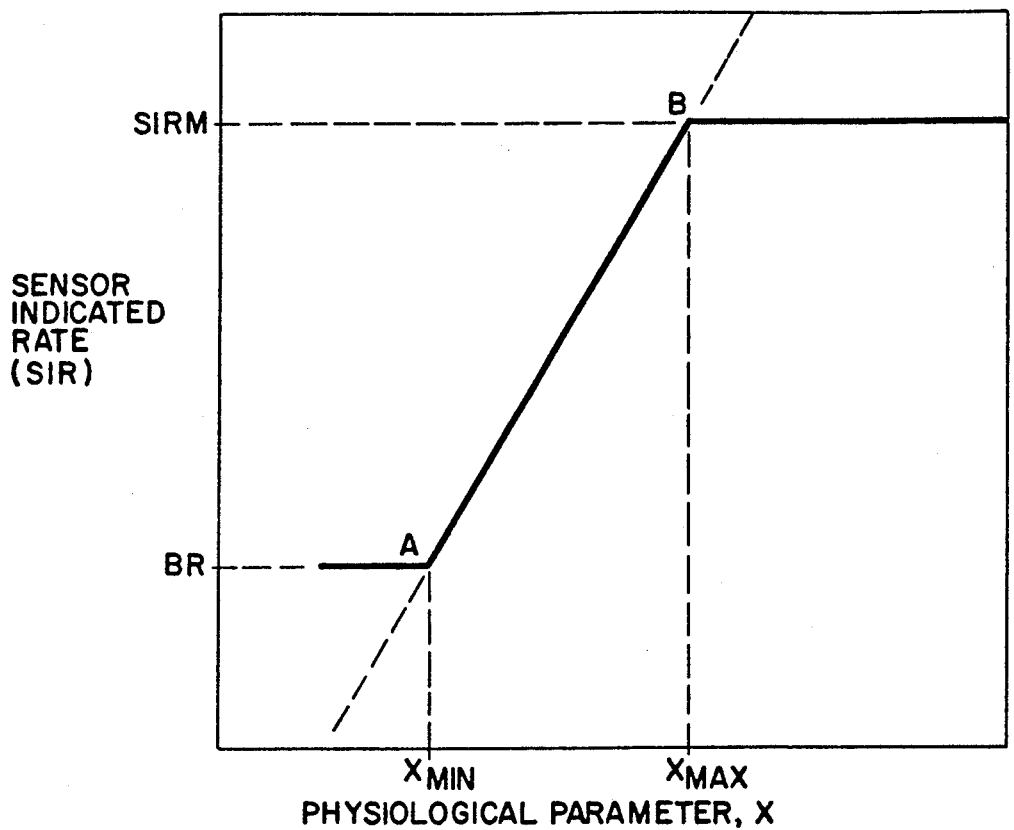
FIG. 7A shows a representative transfer curve of a rate-responsive pacemaker.

In FIG. 7A, a representative transfer function of a rate-responsive pacemaker is illustrated. FIG. 7A is very similar to FIG. 2, but is more general than FIG. 2. The vertical axis of FIG. 7A represents the sensor-indicated pacing rate, identified as SIR, while the horizontal axis represents the physiologic content, of the raw signal from the sensor 24 (FIG. 1), identified as X, corresponding to sensor level index. As indicated in FIG. 7A, there are two points on the transfer curve that significantly influence the operation of the pacemaker. These points include the minimum threshold, Xmin, and the maximum threshold, Xmax.

Figure 8A:
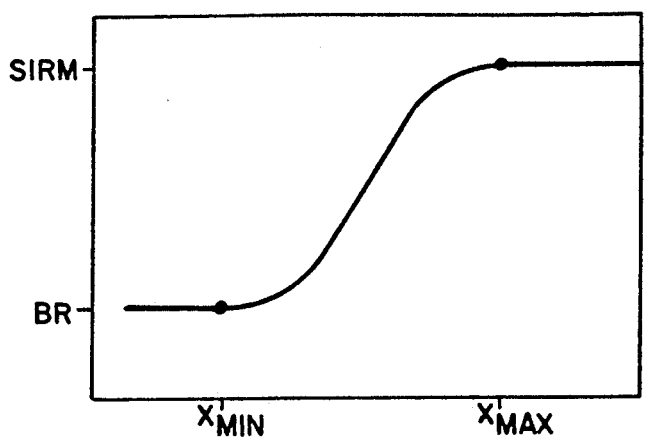
FIGS. 8A, 8B and 8C illustrate transfer curves which are non-linear.
Figure 8B:
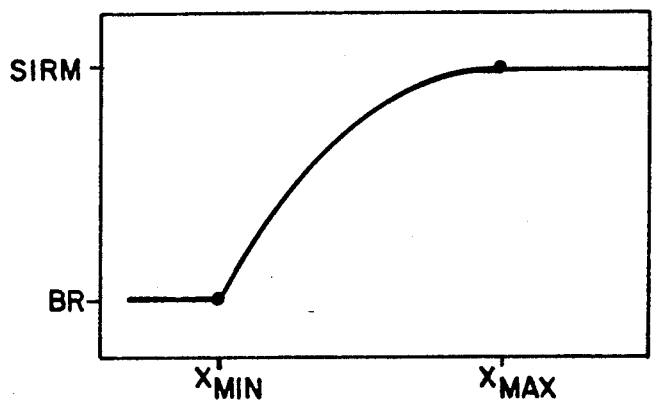
Figure 8C:
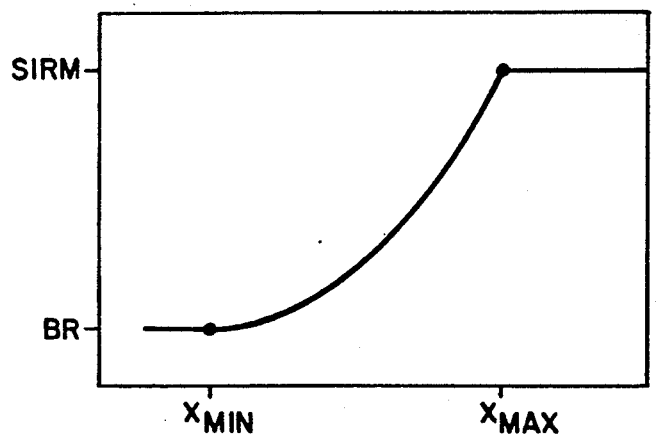

When the rate-responsive mode is selected by the pacemaker (SENSOR ON), the SIR signal controls the rate at which the pulse generator 32 generates stimulation pulses. So long as the content of the sensor signal remains below a minimum value, Xmin, the pacemaker provides stimulation pulses on demand (or as otherwise programmed) at the minimum sensor-indicated rate or base rate, BR. Similarly, so long as the content of the sensor signal remains above a maximum value, Xmax, the pacemaker operates at the maximum pacing rate, SIRM. If, however, the content of the sensor signal lies between Xmin and Xmax, the pacing rate varies as a function of the physiologic content of the raw signal according to a prescribed relationship. This prescribed relationship is depicted in FIG. 7A as a linear relationship. It should be noted, however, that any desired relationship, not just a linear relationship, could be used to relate the physiologic content of the raw signal from the sensor 24 to the pacing rate between the BR and SIRM points. For example, the transfer curve could have a sigmoid relationship, as shown in FIG. 8A, or a low-end or high-end favoring curve, as shown in FIGS. 8B and 8C, or any one of a number of curves programmably selectable by the physician, if so desired. These relationships may be achieved by those skilled in the art in a variety of ways. For example, the transfer operation may be achieved within the processing circuits 26 either algorithmically or by table look-up, as described above.

It should also be noted that the sensor level signals may exceed Xmax and be less than Xmin, as suggested by the dotted line extension of the line A-B in FIG. 7A. However, the processing circuits convert the pacing rate when the sensor level signals are below Xmin to BR, and when the sensor level signals are above Xmax to SIRM. Advantageously, however, the value of any sensor level signal below Xmin or above Xmax may be monitored and calculated into the long-term average for Xmin and Xmax.

With reference to FIG. 7A, an example will now be given of how the operation of the rate responsive pacemaker may be "conditioned" based on the physiological content of the raw signal 54 over a prescribed period of time. At a particular sample time, the physiologic content of the raw signal 54 is determined using a suitable raw signal processor 26. The resulting sensor level signal is stored in memory 28 at a known address as determined by the processing circuit 26. For example, the sensor level signal could be time-logged into memory 28 in a way that identifies the time at which the physiologic sample was taken. Alternatively or conjunctively, an averaged, mean or other representative physiologic signal over a prescribed period of time may be calculated by the processing circuits 26 and stored in memory 28 at a known address. The physiologic signals stored over a relatively long period of time, such as over the past 24 hour period, are then periodically (e.g., once a day) examined by the processor 26. If such examination identifies a significant trend, i.e., an increase or decrease in the physiologic content of the raw signal, then appropriate changes are automatically made, as defined algorithmically or through table look-up, to one or more of the controlling parameters of the rate-responsive pacemaker.

To illustrate this example further, suppose that a long-term trend is identified indicating a general increase in the sensor level of the raw signal, e.g., over several days. Such trend is probably indicative of a long-term increase in the physical activity, and hence physical conditioning, of the patient. For many patients, it would be appropriate to slightly raise Xmin in response to the identification of such a long-term trend. In order to provide added flexibility and versatility in how the rate-responsive pacemaker responds for each unique patient, means are provided whereby the algorithm or table look-up technique (used to define which and how the controlling parameters are affected by a long-term trend identification) may be programmably altered by an attending physician or other medical personnel. Such programming changes are accomplished by techniques known in the art using the pacemaker's telemetry channel circuits and an external programming device.

As described in the example above, the long-term trends that are identified by the processing circuitry 26 (which trends are used to automatically adjust one or more controlling parameters of the pacemaker) are limited to trends associated with the sensor's raw signal as stored in memory 60. It is to be understood, however, that other types of long-term trends could also be identified and used for this purpose. For example, with the availability of modern low power memory circuits, memory 28 could be large enough to store a great deal of data associated with the operation of the pacemaker as well as the heart's natural activity as sensed by the pacemaker. Such data could be processed, either prior to or after storing it in memory 28, for the purpose of identifying other types of trends, such as a long term change in the at-rest or active natural heart rate, the ratio of stimulated heart beats to natural heart beats, etc. Such trends, if identified, could also be used to alter one or more controlling parameters of the rate responsive pacemaker as described above.

Figure 7B:
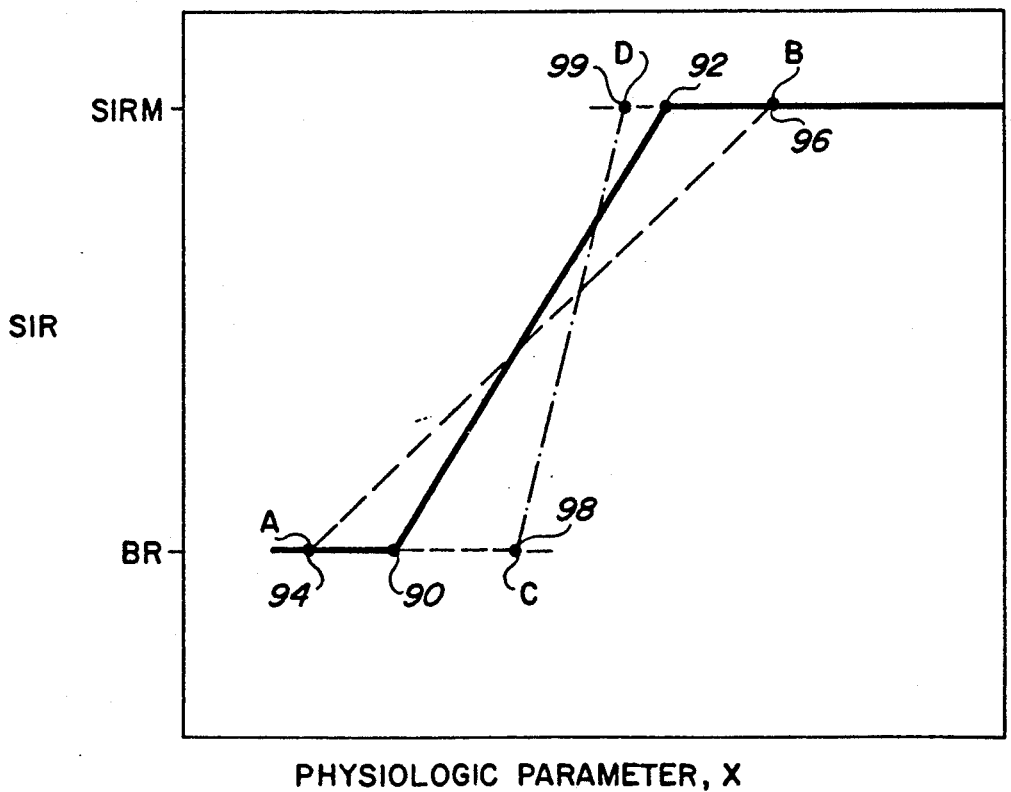
FIG. 7B depicts how the transfer curve of FIG. 7A changes as the minimum and maximum thresholds are adjusted.

In FIG. 7B, a particular example is shown of one manner in which the controlling parameters of the rate-responsive pacemaker are varied or self-adjusted in accordance with one embodiment of the present invention. The controlling parameters varied in FIG. 7B are the minimum value, or Xmin, and the maximum value, Xmax. These values are varied based upon the identification of trends in the sensor level signals over a prescribed period of time, e.g., over the past 12–36 hours. That is, as explained more fully below, the sensor level signals obtained from the physiologic data are monitored over the prescribed period of time. At the conclusion of this time period, at selected times during this prescribed time period or continuously, the sensor signals are examined to compute the average, or other processed value, of the "at rest" or lower sensor level signals, and the "active" or higher sensor signals. Once computed, these averages are then used as the Xmin and Xmax values for subsequent pacing cycles. In this way, the minimum value, Xmin, and maximum value, Xmax, of the pacemaker become self-adjusting, changing as required to fit the particular physiological needs of the patient as determined by the patient's physiological needs sensed during the prior prescribed time period.

Once the Xmin and Xmax values have been adjusted as described above, the appropriate transfer relationship that is used between these limiting points may be any transfer relationship that is appropriate. While a linear relationship is shown in FIG. 7B, it is to be understood that this is only exemplary. Further, as shown in FIG. 7B, it is seen that the programmed baseline, BR, and maximum sensor-indicated rate, SIR, do not change.

Still referring to the example shown in FIG. 7B, assume that the initial value of Xmin and Xmax are as indicated by the points 90 and 92 respectively. In such instance, the transfer relationship becomes the solid line connecting points 90 and 92. If, at the time for adjustment, the average of the "at rest" values occurring during the previous period indicates a value lower than the current Xmin (point 90), then Xmin is adjusted to such lower value, e.g., point 94. If, during this same time period the average of the "active" sensor values over the previous period indicates a value higher than the current Xmax (point 92), then Xmax is adjusted to such higher value, e.g., point 96. The transfer relationship for converting the slope intermediate these two points (94, 96) thus becomes the dashed line A-B. Similarly, if the appropriate averages of the previous sensor values indicates values higher than the current Xmin or lower than the current Xmax, then these values are adjusted to such values, e.g., points 98 or 99, respectively, and the resulting transfer relationship becomes the dashed line C-D.

As FIG. 7B is only intended to illustrate the general principles of how the self-adjusting features of the present invention operate, it will be appreciated that numerous other adjustment possibilities besides those shown in FIG. 7B are possible. For example, if the appropriate previous sensor averages indicate that both Xmin and Xmax should be lowered, then points 94 and 99 would define the adjusted values of Xmin and Xmax, respectively, and a line (or other desired transfer relationship) connecting points 94 and 99 (not shown) would define the controlling transfer relationship.

Figure 9A:
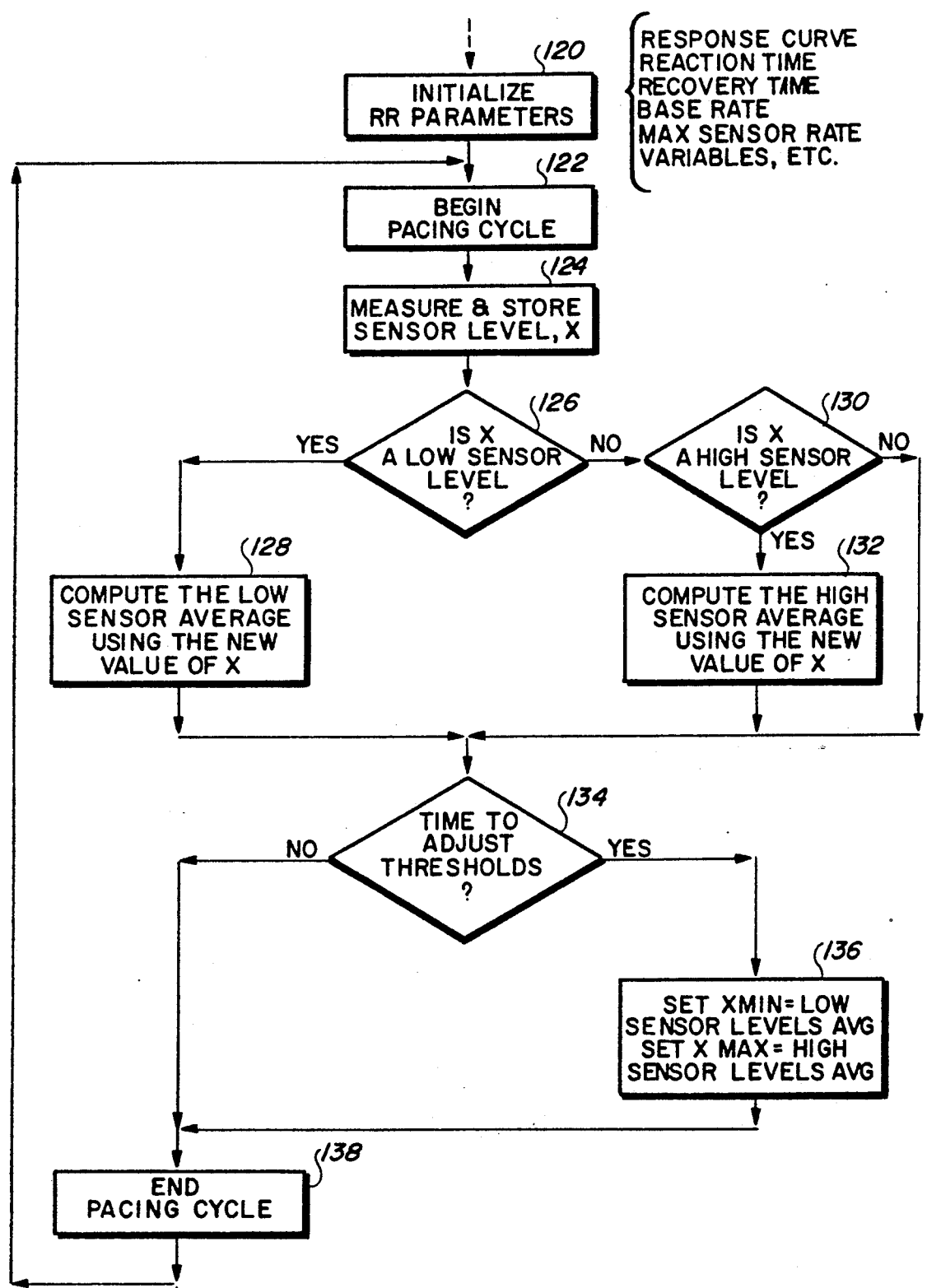
FIG. 9A is a simplified flowchart illustrating the manner in which the minimum and maximum thresholds are automatically self-adjusted in accordance with one embodiment of the invention.
Figure 9B:
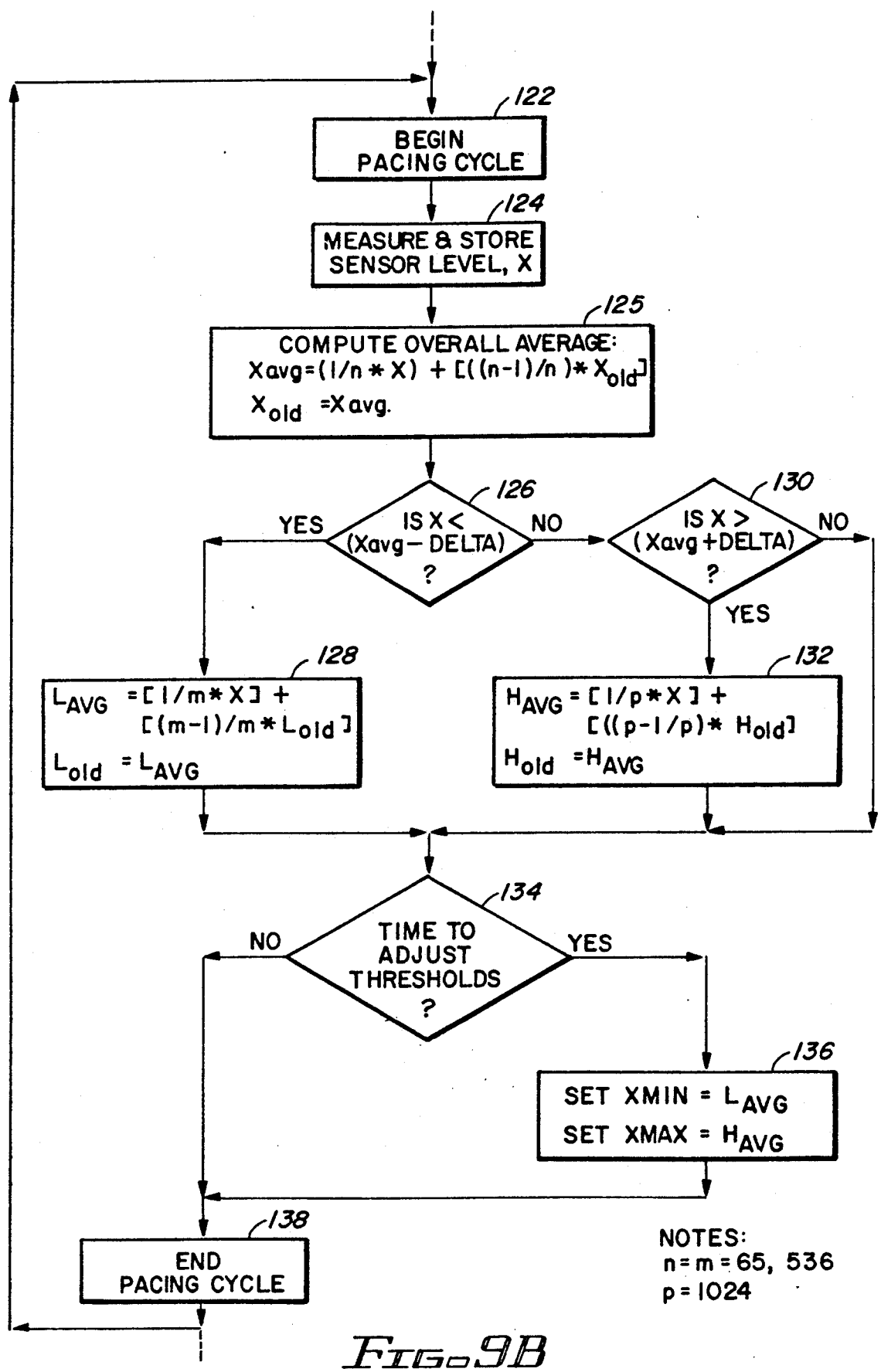
FIG. 9B is an expanded flowchart showing additional detail of a portion of the flow chart of FIG. 9A.

FIG. 9A is a functional flowchart of the detailed flowchart in FIG. 9B. At 120 rate-responsive parameters are initialized. This may include the desired response curve (as shown in FIG. 8A, B or C), the reaction time, the recovery time, base rate, maximum sensor rate, and any appropriate variables. At 122 the pacing cycle begins with a stimulus. During that pacing cycle, the sensor level, X, is measured and stored. At 126 the stored sensor level, X, is compared to a threshold or other indicator to see if it is a low sensor level. If it is, then the current value of X is added to the computation of the low sensor level average at 128. If it is not classified as a low sensor level, it is then tested to see if it is a high level sensor level at 130. If it is, then the value of the stored sample, X, is added to the computation of the high sensor level average. If the sensor level, X, is neither a high nor a low sample (meaning that it could be anywhere in between), the value in this embodiment, is used only to compute or look up a pacing rate between BR and SIRM. In alternate embodiments, the statistics of the intermediate values could be used to determine the entire transfer curve. Next, at 134 the pacemaker looks to see if it is time to adjust the lower and upper thresholds. If it is, then Xmin is set to, or moved toward, the low sensor level average and Xmax is set to, or moved toward, the high sensor level average. Alternatively, Xmin and Xmax could have an offset added to either or both, to reduce false increases about Xmin or inappropriately high rates about Xmax. The pacing cycle then ends at 138 and control loops back to the beginning of the pacing cycle at 122. For subsequent pacing cycles, the new values of Xmin and Xmax are used for the purposes of rate responsive pacing.

In FIG. 9B, the detailed flowchart with the algorithms is shown in complete form. At 122 the pacing cycle begins with the pacing stimulus. At 124 the sensor level, X, is measured and stored in memory.

At 125 the overall average of all the sensor levels over the prescribed period is computed into an average, Xavg. This average is used to discriminate between a low sensor level and a high sensor level. The computation of Xavg is, in the preferred embodiment, a running average which is continuously updated with new sensor levels measured during each pacing cycle. Each new reading of the sensor level, X, has only a small effect on the average, because of the large number of pacing cycles which occur in the prescribed time--in this case, $n = 2^{16} = 65{,}536$. This value of n corresponds to a time constant of approximately 15 ½ hours. The value of "n" was chosen for convenience for implementation in a digital system. At 126 the sensor level, X, is then compared to the average overall sensor level, minus some delta. (Remember that the long-term average, or Xavg, over a period, such as 18 to 24 hours, is a fair representation of the patient's sensor level at rest. This computation, however, does include some high sensor levels included in the average.) By using a small delta, you insure that the high sensor levels and those levels close to the long-term average will be excluded.

At 128 the low average, Lavg, is also shown computed with a similar equation as shown in 125. Since most samples will be low sensor levels, the variable m is also 65,536. If the sensor level, X, is not a low sensor value, then it is compared to the overall average, or Xavg, plus some delta. The delta again is used to discriminate higher sensor levels from the long-term average. If the sample X is a high sensor level, then it is added into the high average, Havg. This equation shown in 132 is similar to the equation for computing the overall average as shown in 125, where p equals 1024. This equates to approximately 15 minutes worth of data. However, it is recognized that these variables—n, m and p—could take on any number of values, depending on the type of sensor used, sampling rate, etc. When it is time to adjust thresholds at block 134, Xmin and Xmax will be set to Lavg and Havg, as described previously. Alternatively, when it is time to adjust thresholds at block 134, Xmin and Xmax can be changed gradually in predefined increments in the directions of Lavg and Havg, respectively. Furthermore, dependent on the direction of the change, the predefined increments for Xmin and Xmax can be varied to provide a faster or slower change in Xmin and Xmax. For example, it may be desirable to rapidly increase Xmax and to slowly decrease Xmax to avoid extended intervals at inappropriately high rates. Alternately, it may be desirable to rapidly reduce Xmin and to slowly increase Xmin to avoid extended intervals at inappropriately low rates. In this manner, each sensor level is classified as being either a low sensor level, intermediate, or a high sensor level. The averages or other processed values of the low sensor levels and the high sensor levels are then used to define the adjusted threshold values for the baseline and the maximum sensor-indicated rate.

Note that by averaging only the selected sensor levels, such average may appropriately be referred to as a weighted average, as it is weighted only by the selected sensor values. Note further that the intermediate values of the sensor levels are not used in the preferred embodiment in computing the lower and upper thresholds. However, it is understood that they are used to determine rates between BR and SIRM and could be used statistically in computing a more appropriate transfer curve for the patient.

It is desirable that the adjustment period be sufficiently long enough to insure that the computed average of the low and high sensor level values be truly representative of the physiologic needs of the patient. Accordingly, sufficient sensor level values should be examined during the adjustment period to insure that the adjustment period is sufficiently long, as indicated previously. However, it is recognized that it could be as few as 12 hours.

While the invention described herein has been described with reference to specific embodiments and applications thereof, numerous variations and modifications could be made thereto by those skilled in the art without departing from the spirit and scope of the invention as claimed.

What is claimed is:

1. A rate-responsive pacemaker comprising:
pulse generator means for generating a pacing pulse at a rate set by a sensor-indicated rate signal;
sensor means for generating sensor signals, the sensor signals varying as a function of sensed physiological activity; and
processor means for generating the sensor-indicated rate signal as a function of the sensor signals at a given sample time, the processor means including means for separately computing first and second averages of the sensor signals from a prescribed number of sample times, being the processor means automatically setting a minimum threshold value and a maximum threshold value as a function of the first and second averages of the sensor signals, respectively, the sensor-indicated rate signal being limited at its low end by the minimum threshold value and being limited at its high end by the maximum threshold value.

2. The rate-responsive pacemaker of claim 1, wherein the first average of the sensor signals comprises an average based on only those sensor signals evidencing activity below a first prescribed threshold level.

3. The rate-responsive pacemaker of claim 2, wherein the first prescribed threshold level comprises an average based on all sensor signals in a prescribed period minus a prescribed delta.

4. The rate-responsive pacemaker of claim 2, wherein the second average of the sensor signals comprises an average based on only those sensor signals evidencing activity above a second prescribed threshold level.

5. The rate-responsive pacemaker of claim 4, wherein the second prescribed threshold level comprises an average based on all sensor signals in a prescribed period plus a prescribed delta.

6. The rate-responsive pacemaker of claim 1, wherein the processing means includes a means for classifying the sensor signals into at least one of two categories, a first category including only those sensor signals evidencing a low level of physiological activity, a second category including sensor signals above the low level of physiological activity, the first average being based upon an average of the sensor signals in the first category.

7. The rate-responsive pacemaker of claim 6, wherein the second category includes only those sensor signals evidencing a high level of physiological activity and wherein the second average is based upon an average of the sensor signals in the second category.

8. The rate-responsive pacemaker of claim 7, wherein the prescribed number of sample times which fall into the second category correspond to at least 5 minutes.

9. The rate-responsive pacemaker of claim 6, wherein the prescribed number of sample times which fall in the first category correspond to at least 12 hours.

10. An implantable pacemaker comprising:
a pulse generator for generating stimulating pulses at a rate set by a rate control signal;
means for generating a bas rate signal;
sensor means for sensing a physiological parameter and for generating a raw sensor signal as a function thereof;
sensor circuit means for generating one of a plurality of sensor level signals as a function of the raw sensor signal;
processing means for generating a sensor-indicted rate signal which varies in a prescribed manner as a function of the sensor level signals, the sensor-indicated rate signal assuming a first minimum value for all sensor level signals below a first prescribed threshold and a second maximum value for all sensor level signals above a second prescribed threshold, the processing means also from automatically adjusting the first prescribed threshold and the second prescribed threshold of the sensor level signals as a prescribed function of selected sensor level signals over a prescribed time period wherein said prescribed function comprises an average value of each of the selected sensor level signals; and
selection means for selecting one of the base rate signals or the sensor-indicated rate signals as the rate control signal for the pulse generator.

11. The pacemaker set forth in claim 10, wherein the prescribed function of selected sensor level signals for the first prescribed threshold of the sensor level signals comprises an average of those sensor level signals occurring during the prescribed time period indicative of periods of low physiological activity.

12. The pacemaker set forth in claim 10, wherein the prescribed function of selected sensor level signals for the second maximum value of the pacing rate signal comprises an average of those sensor level signal occurring during the prescribed time period indicative of periods of high physiological activity.

13. The pacemaker set forth in claim 10, wherein the prescribed function of selected sensor level signals for the first prescribed threshold comprises an average of those sensor level signals occurring during the prescribed time period indicative of periods of low physiological activity and wherein the prescribed function of selected sensor level signals for the second prescribed threshold comprises computing an average of those sensor level signal occurring during the prescribed time period indicative of periods of high physiological activity.

14. The pacemaker set forth in claim 10, wherein the pulse generator includes a housing and wherein the sensor means comprises a piezoelectric sensor secured to the inside of the housing, the sensor signal corresponding to deflections of the housing occurring with patient activity.

15. A self-adjusting rate-responsive pacemaker comprising:
means for generating a pacing pulse on demand at a rate determined by the value of a sensor-indicated rate signal;
physiological sensing means for generating a sensor signal, the rate at which pacing pulses are generated being a function of the value of the sensor signal at any given time;
memory means for storing selected values of the sensor signal over a prescribed period of time;
means for monitoring the sensor signals over the prescribed period of time;
means for classifying the monitored sensor signals over the belonging to one of at least two categories: (1) low sensor signals, or (2) high sensor signals; and
processing means for determining the sensor-indicated rate and a minimum sensor threshold derived from the low sensor signals occurring during the prescribed period of time, the minimum sensor threshold thereafter corresponding to a minimum rate at which the pacemaker generates pacing pulses on demand.

16. The self-adjusting rate-responsive pacemaker as set forth in claim 15, wherein the processing means is for further determining a maximum sensor threshold derived from the high sensor signals occurring during the prescribed period of time, the maximum sensor threshold thereafter corresponding to a maximum rate at which the pacemaker generates pacing pulses on demand.

17. The self-adjusting rate-responsive pacemaker as set forth in claim 16, wherein the maximum sensor threshold is derived from high sensor signals corresponding to at least 5 minutes.

18. The self-adjusting rate-responsive pacemaker as set forth in claim 16, wherein the minimum and maximum sensor threshold signals are adjusted by the processing means at the conclusion of the prescribed period of time.

19. The self-adjusting rate-responsive pacemaker as set forth in claim 16, wherein the minimum and maximum sensor threshold signals re periodically and automatically adjusted by the processing means.

20. The self-adjusting rate-responsive pacemaker as set forth in claim 16, wherein the maximum sensor threshold signal comprises an average of the high sensor signals occurring during the prescribed period of time.

21. The self-adjusting rate-responsive pacemaker as set forth in claim 15, wherein the minimum sensor threshold is derived from low sensor signals corresponding to at least 12 hours.

22. The self-adjusting rate-responsive pacemaker as set forth in claim 15, wherein the minimum sensor threshold signal comprises an average of the lower sensor signals occurring during the prescribed period of time.

23. In a rate-responsive pacemaker having means for generating pacing pulses on demand at a rate determined by the value of a sensor-indicated rate signal, the sensor-indicated rate signal assuming a value at any given time as a function of a sensor signal, the sensor signal being generated by a sensor adapted to sense the need of the pacemaker to change the rate at which pacing pulses are generated, the pacemaker further having sampling means for sampling the values of the sensor signals over time, a method of automatically adjusting a minimum sensor threshold signal, the method comprising the steps of:
(a) sampling the sensor signals over a prescribed period of time;
(b) classifying the stored sensor signals as belonging to one of at least two categories; (1) low sensor signals, or (2) high sensor signals; and
(c) computing a representative value of the low sensor signals and using such representative value as an adjusted minimum sensor threshold signal, wherein pacing pulses are generated on demand at a rate determined by the value of the sensor-indicated rate signal when the sensor signals are above the adjusted minimum sensor signal and at a base rate when the sensor signals are either equal to or below the adjusted minimum sensor signal.

24. The adjustment method as set forth in claim 23, wherein the prescribed period of the time comprises at least 12 hours.

25. The adjustment method as set forth in claim 23, wherein the representative value computed in step (c) comprises an average of the low sensor signals.

26. The adjustment method as set forth in claim 23, wherein the method further includes an automatic adjustment of a maximum sensor threshold signal, the maximum sensor threshold signal defining the maximum rate at which the pacemaker generates pacing pulses on demand, the method including the additional step of:
(d) computing a representative value of the high sensor signals and using such representative value as an adjusted maximum sensor threshold signal, wherein pacing pulses are generated on demand at a maximum rate when the sensor level signals re either equal to or above the adjusted maximum sensor threshold signal.

27. The adjustment method as set forth in claim 26, wherein the representative value of the high sensor signals computed in step (d) comprises an average of the high sensor signals over a second prescribed period of time.

28. The adjustment method as set forth in claim 27, wherein the second prescribed period of the comprises at least 5 minutes.

29. The adjustment method as set forth in claim 28, wherein the computations performed in steps (c) and (d) are performed periodically.

30. A rate-responsive pacemaker comprising:
pulse generator means for generating a pacing pulse at a rate set by a senor-indicated rate signal, the pulse generator mans including a housing;
sensor means, coupled to the housing, for generating sensor signals wherein the sensor means comprises a piezoelectric sensor secured to the housing, the sensor signals varying as a function of the deflection of the housing occurring with physiological activity; and
processor means for generating the sensor-indicated rate signal as a function of the sensor signals at a given sample time, the processor means including mean for separately computing first and second averages of the sensor signals from the prescribed number of sample times, the processor means automatically setting a minimum threshold value and a maximum threshold value as a function of the first and second averages of the sensor signals, respectively, the sensor-indicated rate signal being limited at its low end by the minimum threshold value and being limited at its high end by the maximum threshold value.

* * * * *